United States Patent
Shafiee et al.

(10) Patent No.: US 11,926,809 B2
(45) Date of Patent: Mar. 12, 2024

(54) AUTOMATED EVALUATION OF SPERM MORPHOLOGY

(71) Applicant: THE BRIGHAM AND WOMEN'S HOSPITAL, INC., Boston, MA (US)

(72) Inventors: Hadi Shafiee, Boston, MA (US); Manoj Kumar Kanakasabapathy, Boston, MA (US); Prudhvi Thirumalaraju, Watertown, MA (US)

(73) Assignee: BRIGHAM AND WOMEN'S HOSPITAL, INC., Boston, MA (US)

(*) Notice: Subject to any disclaimer, the term of this patent is extended or adjusted under 35 U.S.C. 154(b) by 449 days.

(21) Appl. No.: 17/281,093

(22) PCT Filed: Sep. 3, 2019

(86) PCT No.: PCT/US2019/049367
§ 371 (c)(1),
(2) Date: Mar. 29, 2021

(87) PCT Pub. No.: WO2020/068380
PCT Pub. Date: Apr. 2, 2020

(65) Prior Publication Data
US 2021/0374952 A1    Dec. 2, 2021

Related U.S. Application Data

(60) Provisional application No. 62/738,157, filed on Sep. 28, 2018.

(51) Int. Cl.
*G06K 9/62* (2022.01)
*C12M 3/06* (2006.01)
(Continued)

(52) U.S. Cl.
CPC ......... *C12M 23/16* (2013.01); *G01N 15/1056* (2013.01); *G06F 18/2431* (2023.01);
(Continued)

(58) Field of Classification Search
CPC ... C12M 23/16; C12M 41/46; G01N 15/1056; G01N 2015/1006; G01N 2800/367;
(Continued)

(56) References Cited

U.S. PATENT DOCUMENTS 7,252,642 B2    8/2007  Kislev et al.
2017/0205390 A1*  7/2017  Shaked .............. G01N 15/1468
(Continued)

FOREIGN PATENT DOCUMENTS

CN    108510504 A    9/2018
EP    2781945 A1    9/2014
(Continued)

OTHER PUBLICATIONS

Van Raemdonck, Lore EM, et al. "An algorithm for morphological classification of motile human sperm." 2015 Sensor Data Fusion: Trends, Solutions, Applications (SDF). IEEE, 2015.
(Continued)

*Primary Examiner* — Xin Jia
(74) *Attorney, Agent, or Firm* — TAROLLI, SUNDHEIM, COVELL & TUMMINO L.L.P.

(57) ABSTRACT

Systems and methods are provided for provided for automatic evaluation of sperm morphology. An image of a semen sample is obtained, and at least a portion of the image is provided to a convolutional neural network classifier. The convolutional neural network classifier evaluates the portion of the image to assign to the portion of the image a set of likelihoods that the portion of the image belongs to a plurality of output classes representing the morphology of sperm within the portion of the image. A metric is assigned to the semen sample based on the likelihoods assigned by the convolutional neural network.

15 Claims, 2 Drawing Sheets

(51) Int. Cl.
  *G01N 15/10*    (2006.01)
  *G06F 18/2431*  (2023.01)
  *G06T 5/30*     (2006.01)
  *G06T 7/00*     (2017.01)
  *G06T 7/11*     (2017.01)
  *G06T 7/136*    (2017.01)
  *G06T 7/73*     (2017.01)
  *G06V 10/34*    (2022.01)
  *G06V 10/80*    (2022.01)
  *G06V 20/69*    (2022.01)
  *H04N 23/55*    (2023.01)
  *H04N 23/56*    (2023.01)

(52) U.S. Cl.
  CPC .............. *G06T 5/30* (2013.01); *G06T 7/0012* (2013.01); *G06T 7/11* (2017.01); *G06T 7/136* (2017.01); *G06T 7/74* (2017.01); *G06V 10/34* (2022.01); *G06V 10/809* (2022.01); *G06V 20/695* (2022.01); *G06V 20/698* (2022.01); *H04N 23/55* (2023.01); *H04N 23/56* (2023.01); *G01N 2015/1006* (2013.01); *G06T 2207/10056* (2013.01); *G06T 2207/20076* (2013.01); *G06T 2207/20081* (2013.01); *G06T 2207/20084* (2013.01)

(58) Field of Classification Search
  CPC ....... G01N 15/1475; G01N 2015/1497; G01N 15/1429; G06F 18/2431; G06T 5/30; G06T 7/0012; G06T 7/11; G06T 7/136; G06T 7/74; G06T 2207/10056; G06T 2207/20076; G06T 2207/20081; G06T 2207/20084; G06T 2207/10048; G06T 2207/20036; G06T 2207/30024; G06T 7/0014; G06V 10/34; G06V 10/809; G06V 20/695; G06V 20/698; G06V 2201/03; H04N 23/55; H04N 23/56; G06N 3/045; G06N 3/08
  See application file for complete search history.

(56)  References Cited

U.S. PATENT DOCUMENTS

2018/0181792 A1    6/2018  Shafiee
2018/0246028 A1*   8/2018  Hsu ................... G01N 15/1475

FOREIGN PATENT DOCUMENTS

| WO | 2017214023 A1 | 12/2017 | | |
| WO | 2018/104819 A1 | 6/2018 | | |
| WO | 2018104819 A1 | 6/2018 | | |
| WO | WO-2018104897 A1 * | 6/2018 | ......... | A61B 10/0058 |
| WO | WO-2020001914 A1 * | 1/2020 | ......... | G06K 9/00127 |

OTHER PUBLICATIONS

Nissen, Malte S., et al. "Convolutional neural networks for segmentation and object detection of human semen." Scandinavian conference on image analysis. Springer, Cham, 2017.

PCT International Search Report and Written Opinion for corresponding International Application Serial No. PCT/US2019/049367, dated Nov. 20, 2019, pp. 1-10.

* cited by examiner

AUTOMATED EVALUATION OF SPERM MORPHOLOGY

RELATED APPLICATIONS

The present application claims priority to U.S. Provisional Patent Application Ser. No. 62/738,157 filed Sep. 28, 2018 entitled AN INEXPENSIVE ARTIFICIAL INTELLIGENCE-BASED SYSTEM FOR SPERM MORPHOLOGY ASSESSMENTS, and the content of this application is incorporated herein by reference in its entirety for all purposes.

TECHNICAL FIELD

The present invention relates generally to the field of medical decision support, and more particularly to automated evaluation of sperm morphology.

BACKGROUND OF THE INVENTION

There are more than seventy million infertile couples worldwide. Approximately one in every four infertile couples seek clinical treatment, where male factor accounts for about fifty percent of the infertility cases. The most important factors for male infertility include low sperm count and motility and sperm abnormality, which reduce the ability of sperm cells for oocyte fertilization. Assisted reproductive technologies (ARTs) such as in vitro fertilization (IVF), intracytoplasmic sperm injection (ICSI), and intrauterine insemination (IUI) are generally utilized in reproductive clinics to treat infertile couples. With an increasing rate of male infertility due to environmental and physiological conditions, there is an ever-growing need for the use of ARTs in reproductive clinics.

There are four main factors which semen analysis tests examine: sperm concentration, sperm morphology, motility, and progressive motility. Sperm concentration tests examine the concentration of sperm in one milliliter (mL) of semen (approximately 20 million sperms/mL) though sperm concentration is not an accurate indicator of a male's ability to reproduce. Males with a low sperm count can still reproduce, and males with high sperm counts can have difficulty. This discrepancy is due to sperm motility, a crucial factor which controls how capable the sperm is of entering an oocyte. Sperm motility, the movement of sperm, must be past a certain threshold in order for the sperm to successfully be able to swim up the female vaginal tract and penetrate the oocyte's hard outer shell. Seminal quality is evaluated by determining the percentage of motile sperm cells and the relative velocity of progressively motile sperm cells in a sample. The progressive motility of a sperm is a fundamental working characteristic that controls its ability to enter into both cervical mucus and the oocyte vestments.

While at-home methods for sperm concentration and motility evaluations have been developed, owing to the complexity of morphology assessments, automated microscopy-based evaluation of sperm morphology at-home has never been possible. Furthermore, all proposed alternative technologies have either been too expensive or inaccurate. An inexpensive, portable and automated sperm morphology assessment tool for point-of-care testing can improve access to care especially in resource-limited settings.

SUMMARY OF THE INVENTION

In accordance with an aspect of the present invention, a method is provided for automatic evaluation of sperm morphology. An image of a semen sample is obtained, and at least a portion of the image is provided to a convolutional neural network classifier. The convolutional neural network classifier evaluates the portion of the image to assign the portion of the image a set of likelihoods representing membership of the portion of the image in each of a plurality of output classes representing the morphology of sperm within the portion of the image. A metric is assigned to the semen sample based on the likelihoods assigned by the convolutional neural network.

In accordance with another aspect of the present invention, a system is provided. The system includes a camera that produces an image of a semen sample and an image processor that segments the image to provide a plurality of image tiles. A convolutional neural network evaluates a subset of the image tiles and assigns, for each of the image tiles, respective likelihoods that the tile belongs to each of the plurality of output classes, each of the plurality of output classes representing the morphology of sperm within the image tile.

In accordance with yet another aspect of the present invention, a system includes a camera that produces an image of a semen sample, a processor, and a non-transitory computer readable medium storing instructions executable by the processor. The executable instructions provide an image processor that segments the image to provide a plurality of image tiles and a convolutional neural network that evaluates a subset of the plurality of image tiles and assigns each of the image tiles to one of a plurality of output classes associating them with the morphology of sperm within the image tile. A sample evaluator records the output of the convolutional neural network and assigns a metric representing the overall morphological quality of the semen sample from the respective outputs for the plurality of image tiles.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
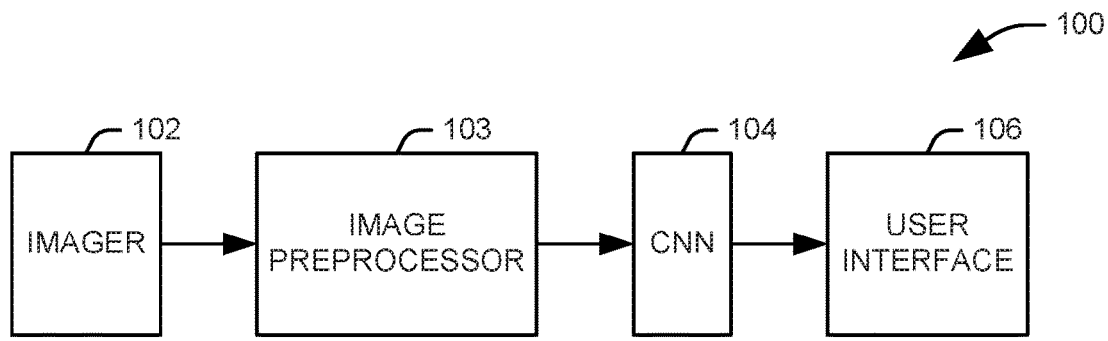
FIG. 1 illustrates a system for automatic evaluation of sperm morphology.

In accordance with an aspect of the present invention, a point-of-care system for evaluating the quality of a semen sample with a mobile device is provided. Men often feel embarrassed to go to urologists, and women carry the weight with regard to infertility. Such behavior and reluctance has created a significantly large market for home-based male infertility tests. Furthermore, healthcare disparities: economic, cultural, societal, geographic, and religious, are major impediments to accessing infertility care worldwide. Infertility in resource-limited settings is a global issue. In addition, while sperm abnormalities are definitive markers for male infertility, they have also been linked to other medical conditions such as diabetes, thyroid disease, Cushing syndrome, liver or kidney disease, and chronic anemia in men. They may also be related to environmental effects and lifestyle effects such as due to smoking, medications, and dietary habits. Accordingly, by facilitating access to point of care evaluation of semen quality, the claims systems and methods can assist in early detection of these disorders.

Manual microscopy based testing and computer-assisted semen analysis (CASA) systems are the current standard methods to measure semen quality, but these methods are labor-intensive, expensive, and laboratory-based. The CASA technique requires highly trained technicians for producing reliable and repeatable results. It also requires bulky microscopy based image analysis systems that significantly limit its point-of-care applications in clinical settings, stud farming, and animal breeding. A majority of fertility clinics and small hospitals, including as many as ninety eight percent in the United States, do not possess CASA platforms available in the market and so use a less accurate and subjective manual method for semen analysis. Manual test results are subjective making it difficult to compare results from different clinics.

Turbidimetry, photon correlation spectroscopy, laser Doppler velocimetry, impedance-based, and holography-based analysis are also used for semen analysis. However, these methods are far from being inexpensive or portable and have not been adopted for home-based or clinical use for semen quality check. Some of these methods only provide sperm concentration and not motility which is an important factor for semen quality check. The lens-free holography-based method involves a complex image reconstruction and processing that is done on a computer connected to the developed device. It also requires a relatively expensive CMOS or CCD sensor that may not be appropriate for home-based or office-based portable semen analysis. Commonly used portable and home-based fertility assays in the market are FertilMARQ and SpermCheck that are colorimetric analyses that use a chemical staining approach for detecting sperm-specific proteins on the sperm head. However, these assays can only measure sperm concentration and not sperm motility.

The systems and methods described herein provide a simple, rapid, inexpensive, home-based male infertility test can shift the paradigm in infertility diagnosis and management in both developed and developing countries. This private, fast, and inexpensive point-of-care test can help men monitor their fertility potency. Specifically, deep neural network classifiers are pretrained with a large set of images for learning normal and abnormal examples of sperm morphology. In one example, a convolutional neural network is applied to identify the variations between morphologically normal and morphologically abnormal sperm. The system is resilient to changes in image illumination and quality due to data acquisition using multiple instruments.

FIG. 1 illustrates a system 100 for automatic evaluation of sperm morphology. The system 100 includes an imager 102 that acquires an image of the semen sample. For example, the imager 102 can include one or more cameras, capable of producing images in the visible or infrared range, paired with appropriate optics to provide an enhanced image of a semen sample. It will be appreciated that the semen sample can be stained or unstained and provided as a fixed smear or in suspension. Staining is performed clinically to enhance the features on sperm cells for visual analysis of morphology. In one implementation, the imager 102 includes an attachment for a mobile device that operates with a camera of the mobile device to provide the images of semen samples. The housing for the attachment can 3-D printed, for example, using polylactic acid, and proportioned to be placed over a mobile device. One or more lenses can be included in the housing to provided appropriate magnification for the images of the semen sample.

In another implementation, the imager 102 can be implemented as a stand-alone system an optical housing containing an electronic circuit with a light source, a power source, and appropriate optics for magnifying the sample. The semen sample can be trans-illuminated or epi-illuminated, with a set of one or more objective lenses for image magnification and an image sensor, for example a complementary metal-oxide-semiconductor (CMOS), for image data acquisition. In one example, the objective lenses include a 4× lens, a 10× lens, and a 40× lens that can be exchanged via a servo motor. The image sensor can be connected to a single-board computer to process the captured images. The imager 102 can be connected to a mobile device via a wireless connection (e.g., Wi-Fi, Bluetooth, or a similar connection) for data processing and visualization.

In either example, either or both of the objective lens and the image sensor can be movable along the optical axis to allow for a selectable distance between the objective lens and the image sensor, which can be used to vary a level of magnification. In one implementation, where both the image sensor and the objective lens can be translated, the objective lens can be moved along the optical axis to attain focus, while the image sensor can be moved independently to select a level of magnification. A sample stage, which holds the semen sample, can be translatable within a plane normal to the optical axis. Accordingly, a portion of the semen sample within the field of view of the image sensor can be selected via translation of the sample stage. In one example, lead screws, driven by a bipolar stepper motor, are used to translate the image sensor and the objective lens along the optical axis. A belt drive mechanism, also driven by the stepper motor, can be used to translate the sample stage. This arrangement can be used to image the semen sample via confocal microscopy.

The one or more images obtained at the imager 102 are provided to an image preprocessor 103 that applies image processing techniques to the captured images to condition the images for analysis at a convolutional neural network (CNN) 104. For example, the images can be reduced to a binary image, an inverted binary image, or a grayscale image, such that some color information is deliberately excluded from the image. Other techniques include dilution, segmentation, filtering the image with low-pass or high-pass filters. In particular, the use of a low-pass filter for reducing noise in the image has been found to be useful in improving the quality of images for morphology analysis. It will be noted, however, that the convolutional neural network 104 can include convolutional layers that replicate several of these image processing functions, and preprocessing of the image is not necessary for a system in accordance with the invention described herein.

The convolutional neural network 104 calculates, from the preprocessed images of the semen sample, at least one output value representing the morphology of the sperm within the image. For example, the convolutional neural network 104 can classify the image into one of a plurality of classes representing normal morphology, abnormal morphology, or a particular type of abnormality (e.g., head defects, midpiece defects, tail defects, missing acrosome, etc.). In this example, the convolutional neural network 104 can be trained on a plurality of images of sperm that have been classified into the selected classes by one or more experts. A convolutional neural network is a feed-forward artificial neural network that includes convolutional layers, which effectively apply a convolution to the values at the preceding layer of the network to emphasize various sets of features within an image. In a convolutional layer, each neuron is connected only to a proper subset of the neurons in the preceding layer, referred to as the receptive field of the neuron. In one implementation, at least one chromatic value (e.g., a value for an RGB color channel, a YCrCb color channel, or a grayscale brightness) associated with each pixel is provided as an initial input to the convolutional neural network.

It will be appreciated that the neural network can be implemented as software instructions stored on a non-transitory computer readable medium and executed by an associated processor. In one implementation, the convolutional neural network 104 can be implemented on a cloud computing system. The convolutional neural network 104 can contain fully-connected layers as well as convolutional and pooling layers, and in one implementation, the network will have at least three convolutional layers followed by one or more fully connected layers.

The results of the neural network 104 can be provided to a user at an associated user interface 106. For example, the user interface 106 can include at least an output device, such as a display, and appropriate software, stored on a non-transitory medium and executed by an associated processor, for receiving the output of the convolutional neural network 104 and presenting it at the output device.

Figure 2:
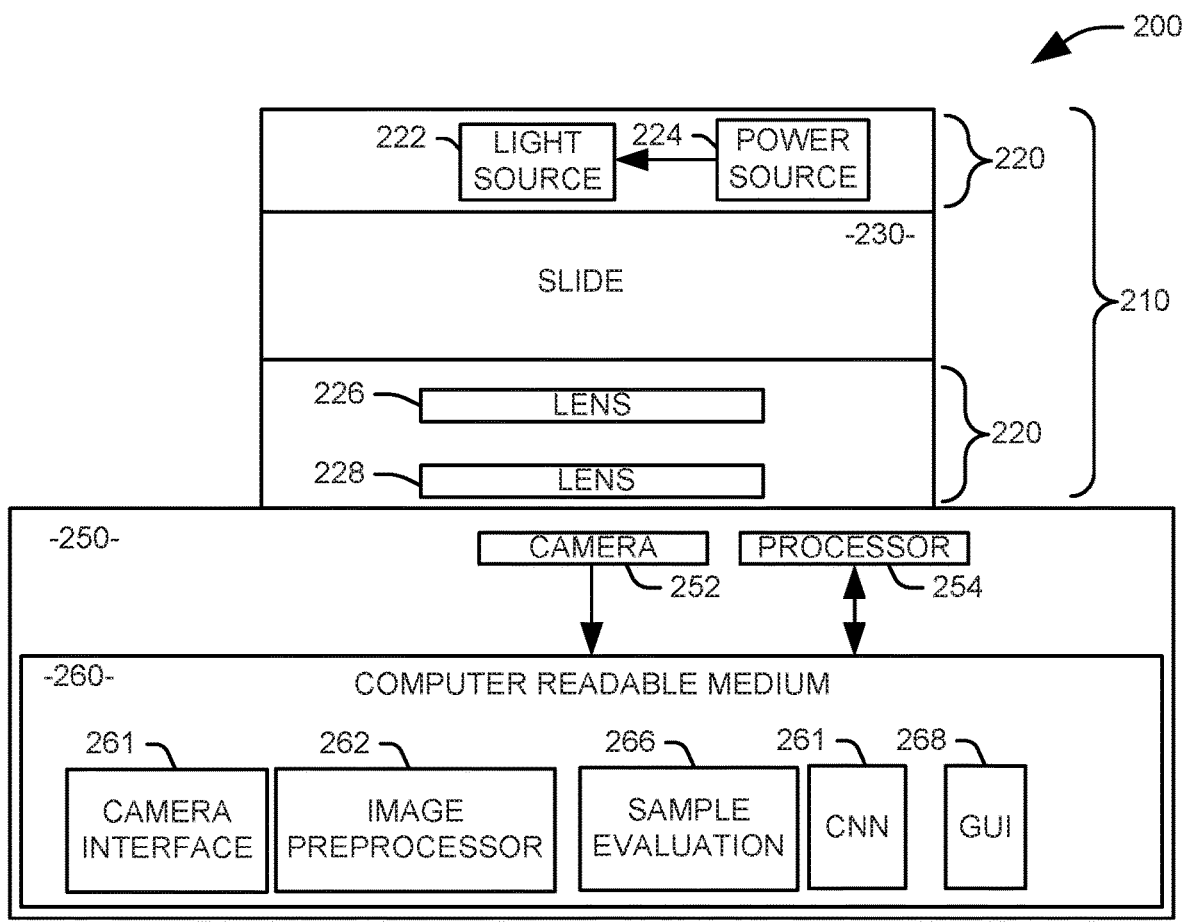
FIG. 2 illustrates one implementation of a system for automated evaluation of sperm quality that includes the capacity for evaluating sperm morphology.

FIG. 2 illustrates one implementation of a system 200 for automated evaluation of sperm quality that includes the capacity for evaluating sperm morphology. In the illustrated implementation, a detachable housing 210 is configured to connect to a mobile device 250, which provides a camera 252 and software for analyzing captured images. It will be appreciated, however, that the system can be implemented as a self-contained assembly that does not require the use of a mobile device. The housing 210 holds an optical assembly 220 comprising at least one lens. In one implementation, the optical assembly 220 includes a light source 222, such as an LED light, a power source 224 for the light source, and two aspheric lenses 226 and 228, arranged to form an optical path along an optical axis of the assembly. It will be appreciated, however, that the housing 210 and optical assembly 220 can be configured to allow a flash on the mobile device to be used as the light source, or to allow a power source associated with the mobile device to power an external light source 222, such that a separate power source 224 is unnecessary.

The housing 210 can be configured to receive a slide 230 to holding the semen sample, either in suspension or as a smear. The slide 230 is configured to engage with the housing 210 such that the reservoir is aligned with the axis of the optical assembly 220. Accordingly, when the microfluidic chip 230 and the housing 210 are in place, the light source will provide transillumination or epi-illumination to the semen sample, and the resulting light will be focused by the at least one lens onto a camera of the mobile device. Captured video of the semen sample can then be used for analysis.

A camera interface 262 is configured to instruct the camera to capture the video. It will be appreciated that this can be done in concert with the analysis of the semen sample, such that the analysis is performed substantially in real-time, or a recording can be stored for later analysis. An image processor 264 is configured to segment the image to provide a plurality of image tiles. In one example, the image processor 264 identifies a plurality of individual sperms within each of a plurality of frames of the video, and each tile contains one or more of the individual sperm. In one implementation, the image processor 264 uses an edge detection algorithm on each frame of video to recognize the individual sperms, such as Canny edge detection or a Sobel filter. Between the magnification provided by the optical assembly 220 and the edge detection algorithm, the image processor 264 can locate objects as small as three micrometers.

Alternatively, the image processor 264 can use other image processing techniques to select tiles for segmentation. For example, the image processor 264 can apply one of dilution and filtering (e.g., high pass or low pass filtering) to the image to generate the representation of the image. These image processing techniques can be applied to the original image or to a representation of the image, generated as one of a binary, an inverse binary, and a grayscale representation of the image. Tiles representing individual sperm or selected groupings of sperm can be provided to the convolutional neural network 261. In still another implementation, a template matching approach can be utilized. In one implementation, the template matching can be performed via a normalized cross-correlation or a sum of absolute differences approach. For example, a cross-correlation between a template representing at least a portion of a sperm and each of a plurality of locations on the image can be computed and locations having a cross-correlation output above a threshold value can be selected. Alternatively, the template matching can be performed using a convolutional neural network trained on template images of sperm.

The convolutional neural network 261 can evaluate the segmented tiles to assign the sperm in the tile to one of a plurality of output classes representing the morphology of sperm within the semen sample. In one implementation, each tile is segmented at the image processor 264 to contain only a single sperm, and the convolutional neural network 261 is trained on individual images of sperm that have been classified into the plurality of classes by human experts. The plurality of output classes can include, for example, a first class comprising morphologically normal sperm and a second class representing morphologically abnormal sperm. Alternatively, the plurality of output classes can include a first class comprising morphologically normal sperm and a plurality of additional classes representing different types of morphologically abnormalities, such as head defects, midpiece defects, tail defects, and missing acrosomes. In one example, the convolutional neural network 261 contains at least three convolutional layers followed by at least one fully connected layer and is implemented on the local computer readable medium 260, although it will be appreciated that the convolutional neural network 261 can be implemented on a remote or cloud server and accessed via a local or wide-area network from a network interface (not shown).

A sample evaluation component 266 determines various metrics indicative of the quality of the semen sample from the data provided by the convolutional neural network 261. The sample evaluator 266 records the one of the plurality of output classes assigned to each of the subset of the plurality of image tiles and assigns a metric representing the overall morphological quality of the semen sample from the recorded output classes for the plurality of image tiles. For example, the metric can be a straightforward percentage of the individual sperm that are determined to fall within an "normal" class, or alternatively, an "abnormal" class. Alternatively, where multiple classes representing abnormal sperm are present, the metric can be determined as a linear combination of respective numbers of the plurality of individual sperm classified into each of the plurality of classes. For example, normal sperm can have a large positive weight, sperm with tail abnormalities can have a small positive weight, and sperm with head defects or missing acrosome can be given a zero or negative weight in the metric.

A graphical user interface (GUI) 268 is configured to provide the results of the semen analysis to the user via a display of the mobile device. For example, the user interface can provide the total number of sperms, a concentration of sperm, a percentage or absolute number of motile sperms, the generated morphology metric, an average linear and/or curvilinear velocity of the motile sperms, and a percentage of the sperms bound by the assay. In addition to an option to begin real-time analysis of a sample, the GUI 269 can provide an option where videos pre-recorded with the cellphone attachment can be analyzed and an option where the user can access the test history. The GUI 269 can also provide a questionnaire where general information about the patient is obtained prior to testing. The user can also gain access through the GUI 269 to further information on how to improve his semen health and the different parameters.

In one implementation, the application can provide feedback to the user based on the analysis on the massive data related to male fertility stored on a cloud system. The stored data may include geographical location, an average humidity and temperature, a humidity and temperature at the time of ejaculation, and user's habits such as smoking, alcohol consumption, etc. The user can utilize this feedback to adjust detrimental environmental or behavioral factors.

Additional supplementary tests can also be merged with this system. For example, by providing an additional weighing scale which can weigh the semen sample and communicate the weight of the sample to the mobile device, the volume of semen produced by the patient can be obtained. An addition of a pH strip to the microchip can determine the pH value of the sample as well. The microfluidic chip 230 can also be augmented with the ability to check for specific biochemical markers using suitable surface chemistry. Such a simplified system capable providing a reliable diagnostic data can help users approach their own healthcare in a proactive manner.

Figure 3:
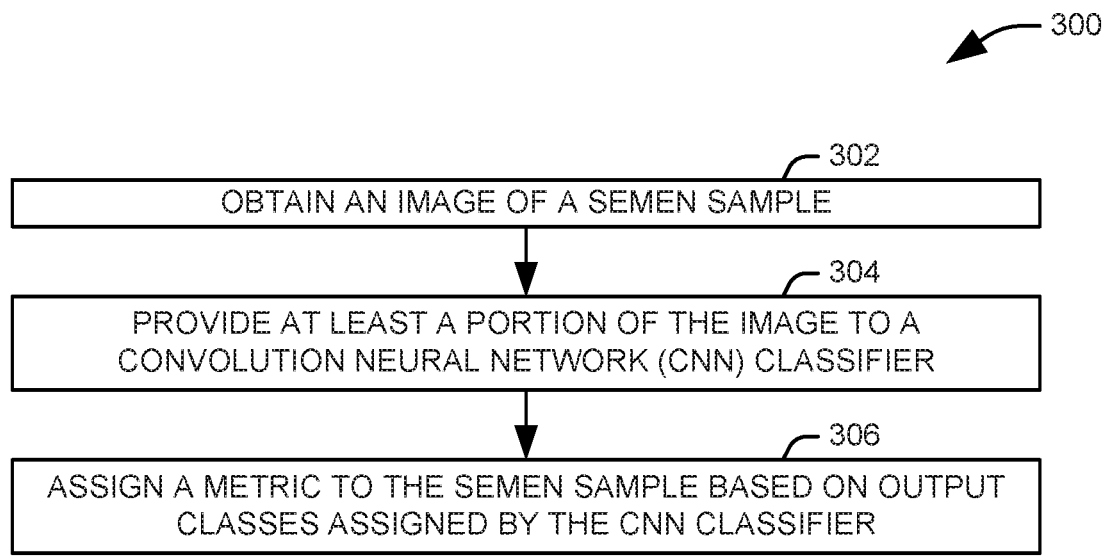
FIG. 3 illustrates a method for automatic evaluation of sperm morphology.

In view of the foregoing structural and functional features described above, a method in accordance with various aspects of the present invention will be better appreciated with reference to FIG. 3. While, for purposes of simplicity of explanation, the methods of FIG. 3 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 3 illustrates a method 300 for automatic evaluation of sperm morphology. At 302, an image of a semen sample is obtained. In one implementation, a camera or other image sensor can be located in a stand-alone unit along with appropriate optics to allow for a magnified image of the semen sample to be captured. In another implementation, a housing with appropriate optics can be configured to be attached to a mobile device, and the camera in the mobile device can be used to capture an image of the semen sample.

At 304, at least a portion of the image is provided to a convolutional neural network classifier. The convolutional neural network classifier evaluates the at least a portion of the image to assign likelihoods that the at least a portion of the image belongs to each of a plurality of output classes representing the morphology of sperm within the semen sample. In one example, the entire image can be provided to the convolutional neural network classifier for evaluation. Alternatively, the image can be segmented to provide a plurality of images of individual sperm or tiles of one or more sperm, which can be classified individually into one of the plurality of output classes at the convolutional neural network. It will be appreciated that the individual sperm can be located within the image or a representation of the image generated as either a binary, an inverse binary, and a grayscale representation of the image. Image processing techniques that can be used in the segmentation can include dilution, high pass filtering, and low pass filtering.

At 306, a metric is assigned to the semen sample based on the one of the output classes assigned by the convolutional neural network. In one example, the metric can represent an overall class assigned to the image by the convolutional neural network. Alternatively, the metric can be a percentage of the sperm classified as normal, or alternatively, a percentage classified as abnormal. In another example, the metric is assigned as a linear combination of respective numbers of the plurality of individual sperm classified into each of the plurality of output classes.

Figure 4:
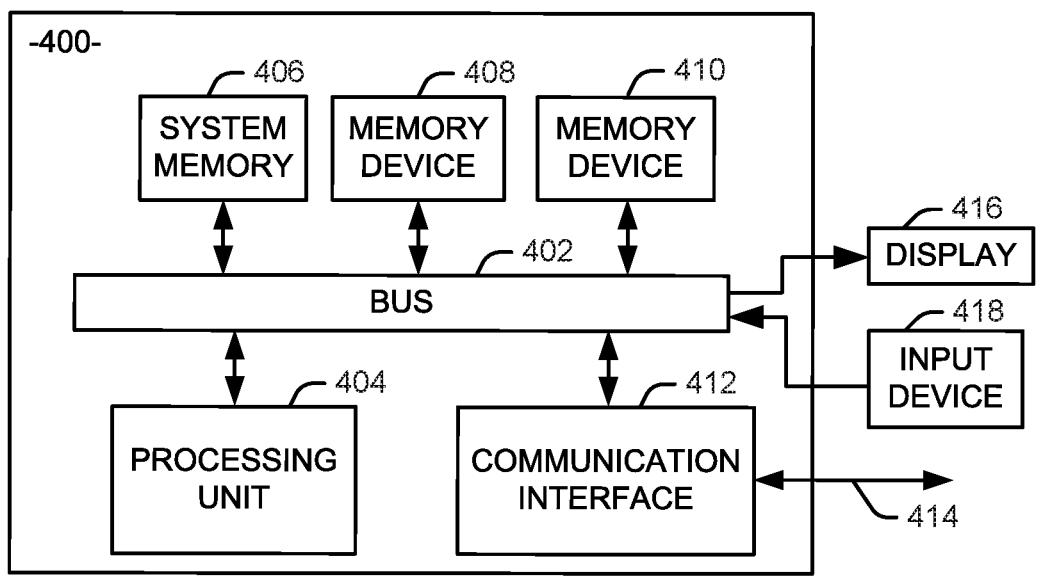
FIG. 4 is a schematic block diagram illustrating an exemplary system of hardware components capable of implementing examples of the systems and methods disclosed herein.

FIG. 4 is a schematic block diagram illustrating an exemplary system 400 of hardware components capable of implementing examples of the systems and methods disclosed in FIGS. 1-3, such as the automated semen evaluation system illustrated in FIG. 1. The system 400 can include various systems and subsystems. The system 400 can be any of personal computer, a laptop computer, a workstation, a computer system, an appliance, an application-specific integrated circuit (ASIC), a server, a server blade center, or a server farm.

The system 400 can includes a system bus 402, a processing unit 404, a system memory 406, memory devices 408 and 410, a communication interface 412 (e.g., a network interface), a communication link 414, a display 416 (e.g., a video screen), and an input device 418 (e.g., a keyboard and/or a mouse). The system bus 402 can be in communication with the processing unit 404 and the system memory 406. The additional memory devices 408 and 410, such as a hard disk drive, server, stand-alone database, or other non-volatile memory, can also be in communication with the system bus 402. The system bus 402 interconnects the processing unit 404, the memory devices 406-410, the communication interface 412, the display 416, and the input device 418. In some examples, the system bus 402 also interconnects an additional port (not shown), such as a universal serial bus (USB) port.

The system 400 could be implemented in a computing cloud. In such a situation, features of the system 400, such as the processing unit 404, the communication interface 412, and the memory devices 408 and 410 could be representative of a single instance of hardware or multiple instances of hardware with applications executing across the multiple of instances (i.e., distributed) of hardware (e.g., computers, routers, memory, processors, or a combination thereof). Alternatively, the system 400 could be implemented on a single dedicated server.

The processing unit 404 can be a computing device and can include an application-specific integrated circuit (ASIC). The processing unit 404 executes a set of instructions to implement the operations of examples disclosed herein. The processing unit can include a processing core.

The additional memory devices 406, 408 and 410 can store data, programs, instructions, database queries in text or compiled form, and any other information that can be needed to operate a computer. The memories 406, 408 and 410 can be implemented as computer-readable media (integrated or removable) such as a memory card, disk drive, compact disk (CD), or server accessible over a network. In certain examples, the memories 406, 408 and 410 can comprise text, images, video, and/or audio, portions of which can be available in formats comprehensible to human beings.

Additionally or alternatively, the system 400 can access an external data source or query source through the communication interface 412, which can communicate with the system bus 402 and the communication link 414.

In operation, the system 400 can be used to implement one or more parts of a sperm evaluation system in accordance with the present invention. Computer executable logic for implementing the composite applications testing system resides on one or more of the system memory 406, and the memory devices 408, 410 in accordance with certain examples. The processing unit 404 executes one or more computer executable instructions originating from the system memory 406 and the memory devices 408 and 410. It will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The terms "computer readable medium" and "machine readable medium" includes, but is not limited to portable or fixed storage devices, optical storage devices, wireless channels, and/or various other storage mediums capable of storing that contain or carry instruction(s) and/or data. It will be appreciated that a "computer readable medium" or "machine readable medium" can include multiple media each operatively connected to a processing unit.

While the principles of the disclosure have been described above in connection with specific apparatuses and methods, it is to be clearly understood that this description is made only by way of example and not as limitation on the scope of the disclosure.

Having described the invention, we claim:

1. A method for automatic evaluation of sperm morphology, comprising:
    obtaining an image of a semen sample;
    segmenting the image to provide a plurality of images of individual sperm;
    providing at least a subset of the plurality of images to a convolutional neural network classifier, the convolutional neural network classifier evaluating the at least a portion of the image to assign respective likelihoods that the at least a portion of the image belongs to each of a set of at least one of a plurality of output classes representing the morphology of sperm within the semen sample and classifying each of the plurality of individual sperm into one of the plurality of output classes at the convolutional neural network based on the assigned likelihoods, the plurality of output classes including at least one class representing normal sperm and at least two classed representing abnormal sperm; and
    assigning a metric to the semen sample based on the likelihoods assigned by the convolutional neural network as a linear combination of respective numbers of the plurality of individual sperm classified into each of the plurality of output classes.

2. The method of claim 1, further comprising applying one of dilution and filtering to the image prior to segmenting the image.

3. The method of claim 2, wherein comprising applying one of dilution and filtering to the image comprises applying a low pass filter to the image.

4. The method of claim 1, further comprising generating one of a binary, an inverse binary, and a grayscale representation of the image prior to segmenting the image.

5. The method of claim 1, wherein segmenting the image comprises applying a template matching process to the imager to locate the individual sperm.

6. The method of claim 5, wherein the template matching process comprises computing a cross-correlation between a template representing at least a portion of a sperm and each of a plurality of locations on the image and selecting locations having a cross-correlation output above a threshold value.

7. The method of claim 5, where the convolutional neural network is a first convolutional neural network and the template matching process comprises providing the image to a second convolutional neural network training on template images of sperm.

8. A system comprising:
   a camera that produces an image of a semen sample;
   an image processor that segments the image to provide a plurality of image tiles, the image processor locating individual sperm within a representation of the image generated via an template matching process in which a cross-correlation between a template representing at least a portion of a sperm and each of a plurality of locations on the image is computed and locations having a cross-correlation output above a threshold value are selected and generating a plurality of tiles from the image according to the locations of the individual sperm; and
   a convolutional neural network that evaluates a subset of the plurality of image tiles and assigns to each of the image tiles to one of a plurality of output classes respective likelihoods that sperm within the image tile belongs to each of a set of at least one of a plurality of output classes representing the morphology of sperm within the image tile.

9. The system of claim 8, wherein the convolutional neural network contains at least three convolutional layers followed by at least one fully connected layer.

10. The system of claim 8, further comprising an optical system that works in conjunction with the camera to produce the image of the semen sample, the optical system comprising:
   a light source; and
   at least one objective lens positioned between the semen sample and the camera.

11. The system of claim 8, wherein the camera is part of a mobile device, and the system further comprises a plastic housing containing an acrylic lens and configured to affix to the mobile device, such that the acrylic lens is aligned with a camera of the mobile device.

12. The system of claim 8, wherein the plurality of output classes includes a first output class comprising morphologically normal sperm and a second output class representing morphologically abnormal sperm.

13. The system of claim 8, wherein the plurality of classes includes a first output class comprising morphologically normal sperm and a plurality of additional output classes representing different types of morphologically abnormalities.

14. The system of claim 8, further comprising a sample evaluator that records the likelihoods assigned to each of the subset of the plurality of image tiles and assigns a metric to the semen sample as a weighted linear combination of respective numbers of the plurality of image tiles classified into each of the plurality of output classes.

15. A system comprising:
   a camera that produces an image of a semen sample;
   a processor; and
   a non-transitory computer readable medium storing instructions executable by the processor to provide an image processor that locates individual sperm within a representation of the image generated via an image processing technique in which a cross-correlation between a template representing at least a portion of a sperm and each of a plurality of locations on the image is computed and locations having a cross-correlation output above a threshold value are selected and generating a plurality of tiles from the image according to the locations of the individual sperm, a convolutional neural network that evaluates a subset of the plurality of image tiles and assigns each of the image tiles to one of a plurality of output classes, including a normal class and at least two abnormal classes, representing the morphology of sperm within the image tile, and a sample evaluator that records the one of the plurality of output classes assigned to each of the subset of the plurality of image tiles and assigns a metric representing the overall morphological quality of the semen sample from the recorded output classes for the plurality of image tiles as a linear combination of respective numbers of the plurality of individual sperm classified into each of the plurality of output classes.

* * * * *